United States Patent [19]

Bonner

[11] Patent Number: 4,522,494
[45] Date of Patent: Jun. 11, 1985

[54] NON-INVASIVE OPTICAL ASSESSMENT OF PLATELET VIABILITY

[75] Inventor: Robert F. Bonner, Washington, D.C.

[73] Assignee: The United States of America as represented by the Department of Health and Human Services, Washington, D.C.

[21] Appl. No.: 396,057

[22] Filed: Jul. 7, 1982

[51] Int. Cl.³ .................. G01N 33/48; G01N 21/53
[52] U.S. Cl. .................................... 356/39; 356/338
[58] Field of Search .............................. 356/39–42, 356/338; 250/574, 576, 564, 565

[56] References Cited

U.S. PATENT DOCUMENTS

| | | | |
|---|---|---|---|
| 3,527,542 | 9/1970 | Penhasi et al. | 356/40 X |
| 3,830,569 | 8/1974 | Meric | 356/39 |
| 4,139,303 | 2/1979 | Carlson et al. | 356/39 |
| 4,178,103 | 12/1979 | Wallace | 356/338 X |
| 4,227,814 | 10/1980 | Soodak et al. | 356/39 X |

Primary Examiner—Vincent P. McGraw
Attorney, Agent, or Firm—Browdy and Neimark

[57] ABSTRACT

A system for assessing platelet viability in a transparent flexible bag. The apparatus employed consists of a support for clampingly receiving the bag and defining an optically exposed constricted region in the bag. A laser beam is passed perpendicularly through the constricted region of the bag. The opposite side portions of the bag are alternately periodically compressed and released to provide laminar fluid flow through the constricted region to align platelet discs face-on with respect to the beam. Scattered light from the beam is passed through an annular gate, defining a selected scatter angle relative to the beam axis. The selected scattered light is directed by a lens onto a photodiode detector. The output of the detector is processed and furnished to a computer, which is employed to derive respective quantities indicating the concentration of non-aggregated platelets and the percentage that are discs. These quantities are obtainable by (1) averaging the output during a period when said laminar flow is provided, to obtain a value $I_l$, and (2) stopping the periodic compression and allowing the platelets to thereafter become randomly oriented, to obtain a value $I_o$. The quantity representing disc percentage is calculated for $(I_l - I_o)/I_o$, whereas the concentration of non-aggregated platelets is calculated from $I_o$.

17 Claims, 6 Drawing Figures

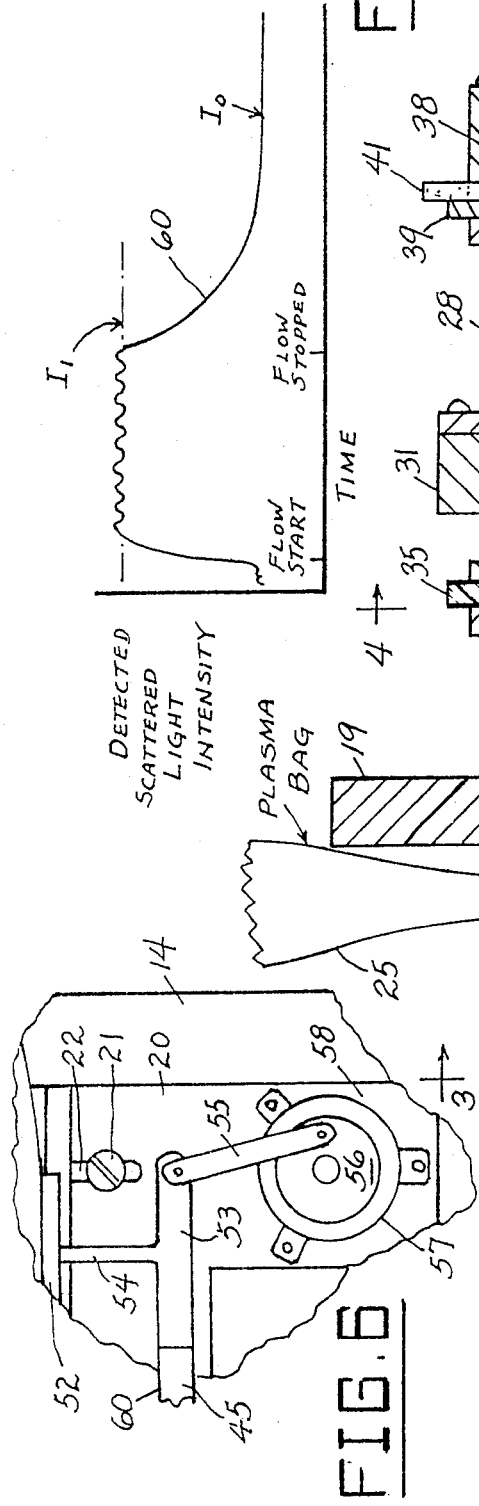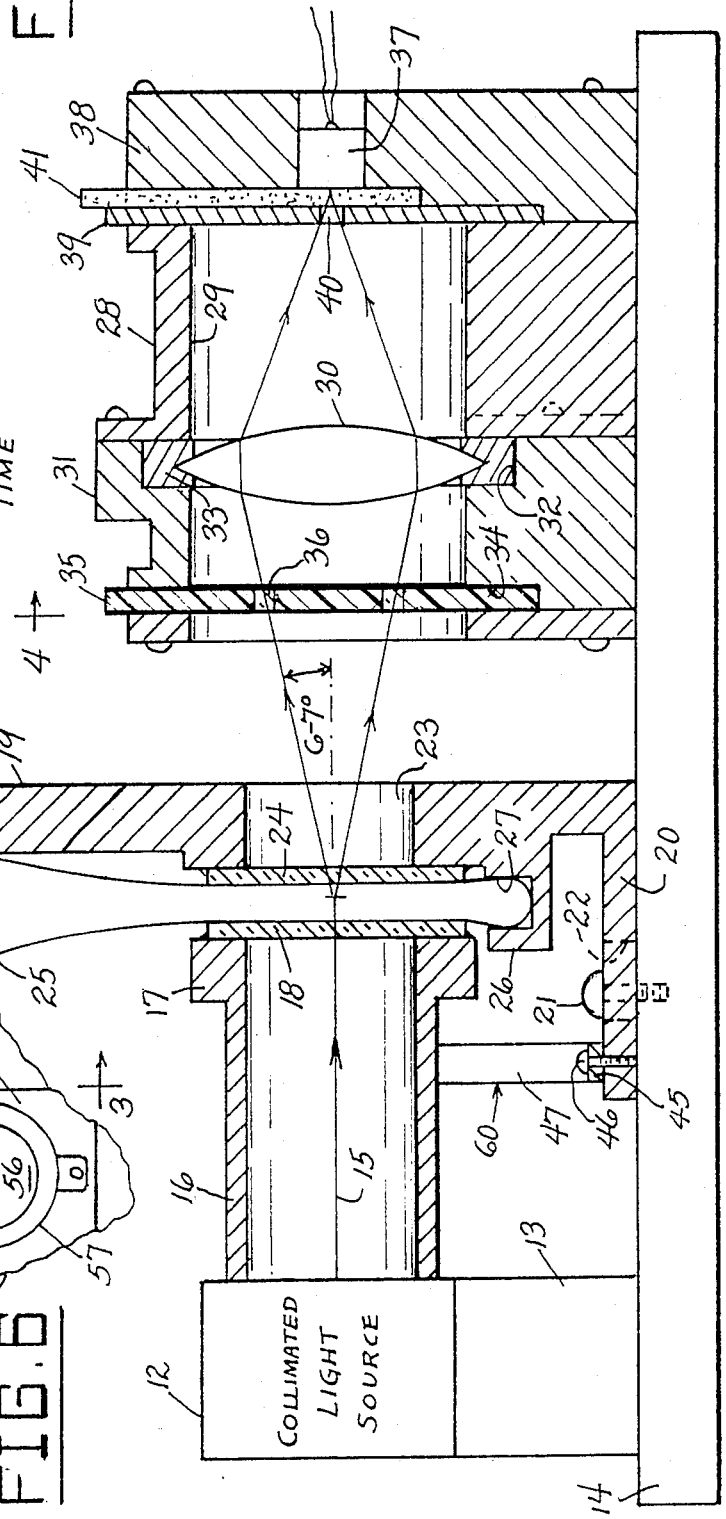

NON-INVASIVE OPTICAL ASSESSMENT OF PLATELET VIABILITY

FIELD OF THE INVENTION

This invention relates to blood platelet testing apparatus, and more particularly to a system for measuring the concentration of non-aggregated platelets and the percentage that are discs, directly within a plastic blood storage bag to be used for furnishing platelets to a patient.

BACKGROUND OF THE INVENTION

The prior method of determining the concentration of non-aggregated platelets and the fraction that are discs, in platelet-rich plasma to be transfused to a patient, is to invasively remove a sample from the transfusion bag and then (1) dilute an aliquot to a high degree (3000:1), which is then counted on an automatic cell counter to give platelet concentration, and (2) to observe visually in a phase microscope a portion of the undiluted sample and subjectively determine (count) the fraction of the platelets that are discs. These combined procedures require the use of at least two expensive pieces of equipment by a highly skilled technician and require at least 30 minutes per sample. Thus, it is a very costly procedure. Furthermore, one is not allowed to routinely sample a transfusion product due to the risk of contamination. For these reasons platelet-rich plasma is usually not checked prior to transfusion to insure good quality, and the quality of transfused platelets is often very poor. There is a definite need for an improved method and apparatus which allows accurate quantitation of the platelet concentration and of the percentage or fraction that are discs, without risk of contamination, using a moderately priced instrument for a short period, for example, about 2 minutes, and being within the range of skill of a relatively inexperienced aid or technician, and thus to enable routine assessment of all bags of platelet-rich plasma which are to be employed for transfusion. Such an improved method and apparatus would enable usage of supplies of platelets which are beginning to show signs of slight functional deterioration but which are still useful, whereas patients would not be transfused with platelets found to be non-functional and useless.

A preliminary search of the prior art revealed the following U.S. patents of interest:

Hogg, U.S. Pat. No. 3,893,766
Breddin et al, U.S. Pat. No. 4,066,360
Frazer et al, U.S. Pat. No. 4,070,113
Kent et al, U.S. Pat. No. 4,135,818
Carlson et al, U.S. Pat. No. 4,139,303
Ehrly, U.S. Pat. No. 4,201,470
Stohr, U.S. Pat. No. 4,243,318
Haina et al, U.S. Pat. No. 4,252,438

SUMMARY OF THE INVENTION

A typical apparatus according to the present invention comprises a HeNe laser rigidly coupled to an optical rail having a parallel-plate transfusion bag holder with parallel glass windows centered on and perpendicular to the laser axis, and a coaxial annular collecting light gate located to define a desired scattering angle, followed by a lens which images the illuminated sample onto a photodiode. The photodiode electrical output is amplified and digitally sampled. A means (either manual or mechanical) is provided for periodic compression of the edges of the transfusion bag in order to force fluid to flow laminarly through the parallel-walled observation gap. This flow results in fluid shear in the direction of the laser beam, which aligns disc-shaped platelets to positions substantially face-on to the laser beam.

A cycle of operation consists of (1) insertion of the transfusion bag between the parallel glass plates, (2) clamping the bag between the parallel plates in order to restrict flow through the parallel gap, (3) periodic compression and release of alternate (opposite) edges of the bag, which results in laminar flow and maximal face-on orientation of the discoid platelets every half cycle; (4) the signal at maximum orientation during 10 seconds of periodic compression is averaged ($I_1$). (5) The compression is stopped, leading to a gradual randomization of platelet orientation by Brownian diffusion; 30 seconds after cessation of flow a 5-second average of the scattered intensity ($I_0$) is obtained for the randomly oriented platelets. (6) Utilizing a computer program based on a multiple scattering theory and on empirical data, the $I_0$ value is used to obtain the platelet concentration within the bag (the behavior of $I_0$ is very different from Beer's law and has not previously been described or explained). Similarly, the fractional change of intensity on orienting the platelets $(I_1-I_0)/I_0$ is used with corrections based on $I_0$ to compute the fraction of platelets that are discs. These computed numbers are read out, and the cycle may be repeated.

Accordingly, a main object of the invention is to provide an improved method and means to measure the concentration of nonaggregated platelets and the fraction that are fully viable or discoid, non-invasively in a plastic blood storage bag, which overcomes the deficiencies and disadvantages of previous techniques employed for this purpose.

A further object of the invention is to provide an improved technique for inspecting the contents of blood storage bags which is non-invasive, which does not cause contamination of the blood product, which employs relatively inexpensive equipment, and which can be reliably and quickly performed by relatively unskilled personnel.

A still further object of the invention is to provide an improved apparatus for optically inspecting blood storage bags to determine the concentration of non-aggregated platelets and the fraction that are discs, non-invasively and directly within the blood storage bag, whereby to determine whether serious functional deterioration has occurred and to avoid transfusing a patient with a non-functional and useless product.

A still further object of the invention is to provide an improved optical inspection apparatus for use with blood storage bags, wherein the bags are clamped between transparent plates perpendicular to a collimated inspection beam to define a restricted flow gap and wherein the outer portions of the bag are periodically compressed and released, resulting in laminar flow through said gap, with maximal face-on orientation of the discoid platelets relative to the inspection beam every half cycle of compression, the scattered light from the platelets being at a selected low scattering angle providing accurate quantitation of the measurements given by the apparatus.

A still further object of the invention is to provide an improved optical inspection apparatus for use with blood storage bags which monitors and evaluates platelet concentration in platelet-rich plasma, which assesses the fraction of the platelets that are viable, which measures a scattering property of the suspension of platelets that could be used for such evaluation, and which provides means for comparing the scattering property of oriented platelets with the scattering property of randomly oriented platelets, as required for determining the fraction of platelets that are discoid (viable).

BRIEF DESCRIPTION OF THE DRAWINGS

Further objects and advantages of the invention will become apparent from the following description and claims, and from the accompanying drawings, wherein:

FIG. 2 is a longitudinal vertical cross-sectional view of a blood platelet testing system according to FIG. 1.

FIG. 5 is a graph showing a typical curve of scattered light intensity versus time obtainable with a blood storage bag by the use of the testing apparatus of the present invention.

FIG. 6 is a fragmentary horizontal plan view taken substantially on line 6—6 of FIG. 3.

DETAILED DESCRIPTION OF A PREFERRED EMBODIMENT

Figure 1:
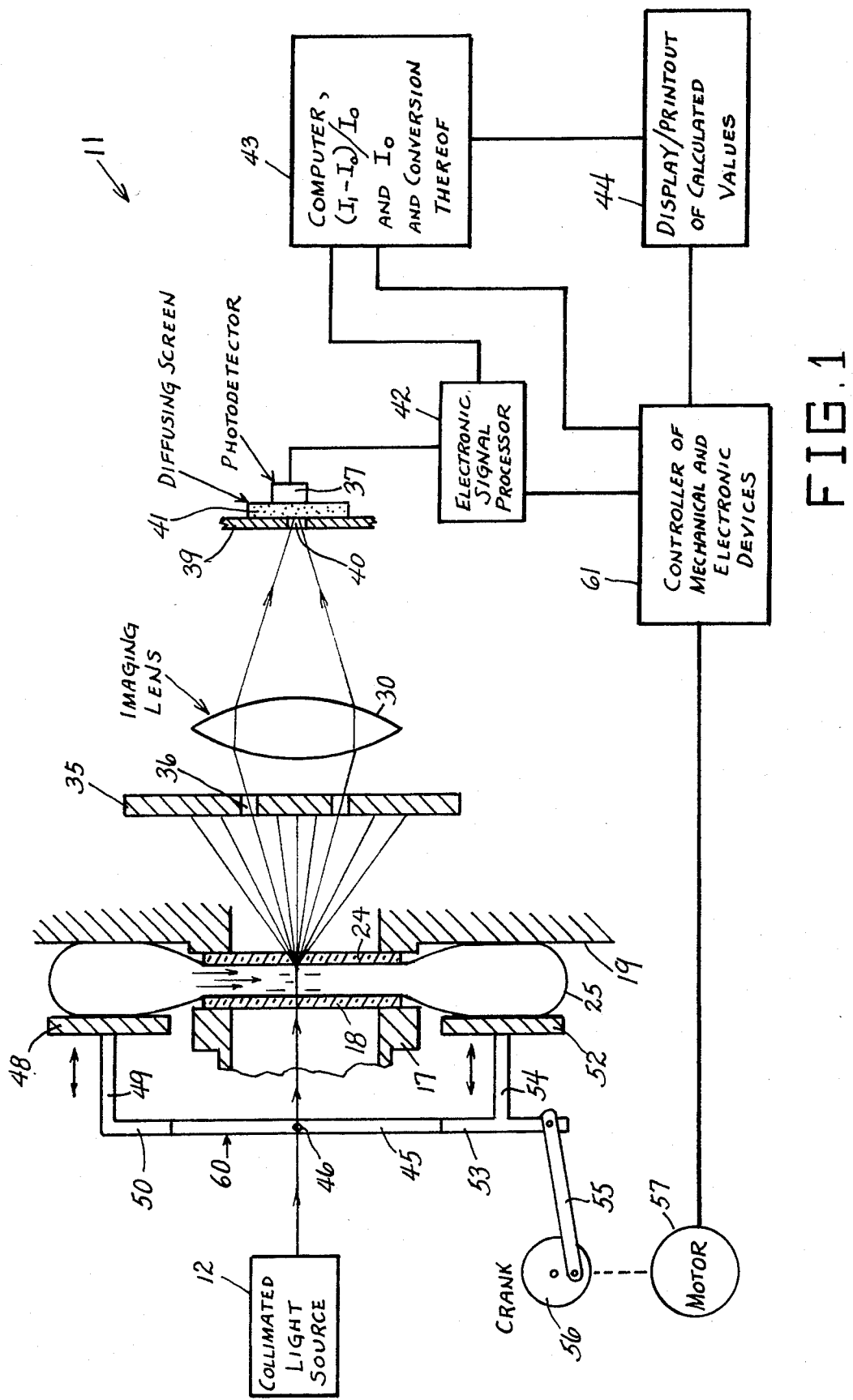
FIG. 1 is a partly diagrammatic horizontal cross-sectional view of a blood platelet testing system according to the present invention.
Figure 3:
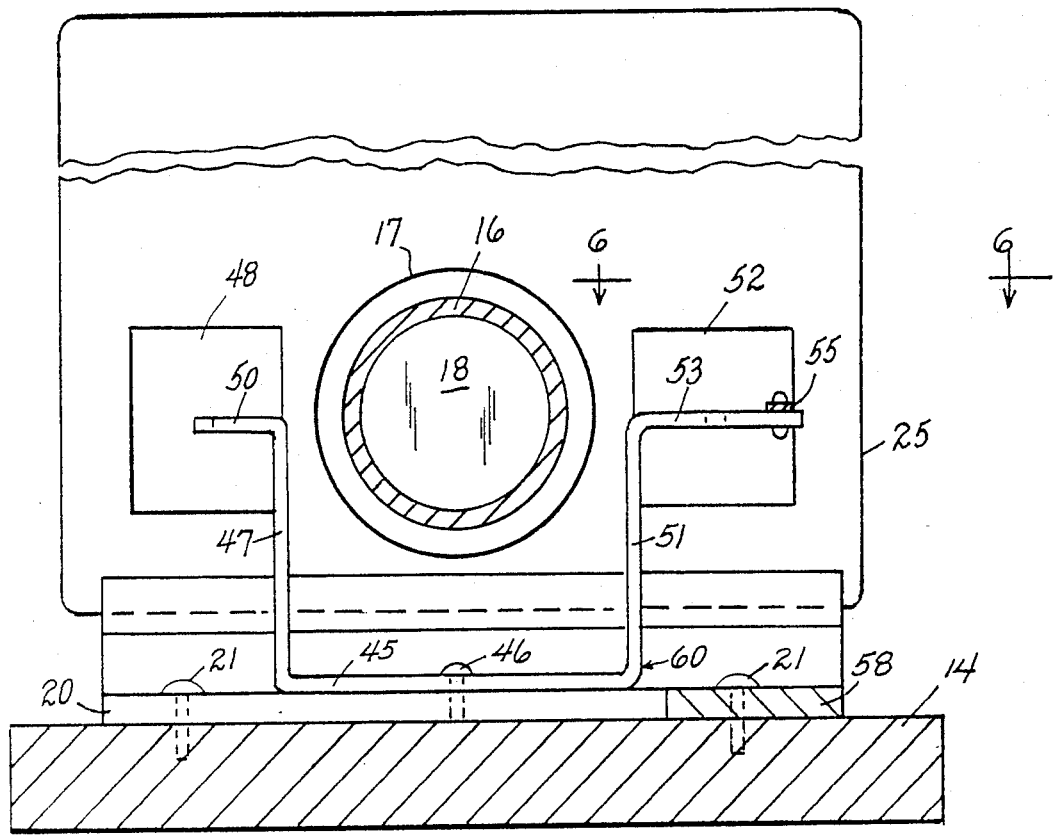
FIG. 3 is a transverse vertical cross-sectional view taken substantially on line 3—3 of FIG. 2.

Referring to the drawings, 11 generally designates a typical blood platelet testing apparatus according to the present invention. The apparatus 11 comprises a collimated light source 12, such as a HeNe laser, rigidly mounted on a support block 13 which is fixedly secured on a base plate 14, the source 12 being mounted with its optical axis horizontal, providing a collimated beam, shown diagrammatically at 15, said beam being coaxially contained in a horizontal guide tube 16 rigidly connected to the housing of light source 12. Tube 16 is provided with a front flange 17 to which is cemented a transparent glass cover plate 18, substantially centered on and being perpendicular to the optical axis defined by beam 15.

Adjustably mounted on the base plate 14 forwardly of and parallel to flange 17 is an upstanding bracket 19 having a base flange 20 supported on base plate 14 and adjustably secured thereto by clamping screws 21, 21 engaged through respective longitudinal slots 22 formed in base flange 20, said clamping screws 21 being threadedly engaged in base plate 14. Bracket 19 is formed with a circular aperture 23 axially aligned with guide tube 16. A transparent glass cover plate 24 is cemented to the leftward face of bracket 19, as viewed in FIG. 2, covering the aperture 23, arranged parallel to glass plate 18 and defining a clamping space therebetween in which a conventional transparent plasma bag 25 is receivable, as shown in FIG. 2. Bracket 19 is integrally formed with a horizontal flange or shelf 26 underlying said clamping space and formed with an upwardly facing seat or groove 27 in which the bottom edge portion of the conventional plasma bag 25 is supportingly receivable.

Figure 4:
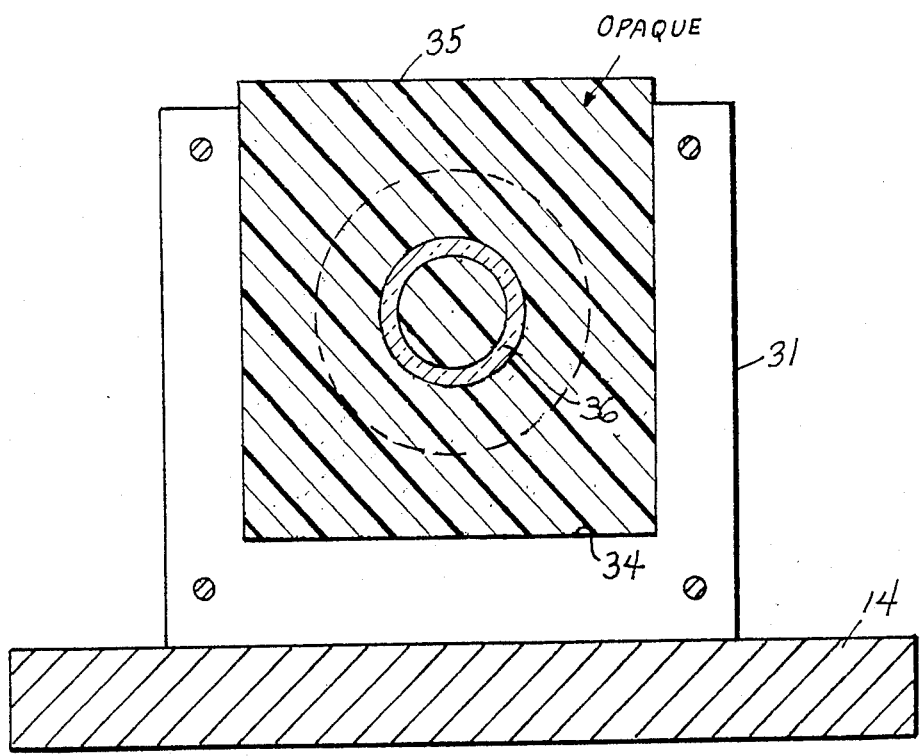
FIG. 4 is a transverse vertical cross-sectional view taken substantially on line 4—4 of FIG. 2.

Designated at 28 is an upstanding optical block rigidly secured on base plate 14 and having an optical guide bore 29 axially aligned with guide tube 16. A lens 30 is rigidly clamped to the leftward rim of bore 29, as viewed in FIG. 2, by a lens clamping block 31 having an annular recess 32 which receives an annular retaining ring 33 in which the lens 30 is mounted, as shown in FIG. 2. The leftward portion of block 31 is recessed at 34 to define a rectangular seat in which a vertical light gate member 35 is receivable and by which it is positioned in optical alignment with the aperture 23. Light gate member 35 comprises a plate-like rectangular body which is opaque, except for an annular transparent portion 36 (see FIG. 4), which is supported so as to be coaxial with the common optical axis of beam 15 and of lens 30. The light gate 35 is located so that annular portion 36 defines a desired selected scattering angle with respect to light scattered by platelets in the plasma contained in bag 25, as will be presently described, for example, a scattering angle of between 6° and 7° from the forward beam axis. The lens 30 images the illuminated sample onto a photodiode 37 mounted coaxially with lens 30 in an upstanding supporting block 38 secured to the rightward end face of block 28, as viewed in FIG. 2. Block 38 is recessed to supportingly receive an opaque plate member 39 with a viewing aperture 40 aligned with photodiode 37. Block 38 is also recessed to receive a translucent diffusing screen 41 between viewing aperture 40 and photodiode 37. The scattered-light image of the illuminated sample is thus transmitted by lens 30 to the photodiode 37 via aperture 40 and the diffusing screen 41. The photodiode electrical output is amplified and processed in an electronic signal processor 42 (FIG. 1) and a computer 43, and is read out and/or recorded in a conventional display and printout device 44. In a simple form of the system, said photodiode electrical output can be amplified and then read out on a voltmeter and recorded on a chart recorder.

A mechanism is provided for periodic compression of the side marginal portions of the plasma transfusion bag 25 in order to force fluid to flow laminarly through the parallel-walled observation space in transparent bag 25 defined between the glass plates 18, 24. This flow results in fluid shear in the direction of the laser beam 15, which aligns disc-shaped platelets to positions substantially face-on to the laser beam. A typical compression mechanism comprises a generally U-shaped bar member 60 having a linear bight portion 45 centrally pivotally connected at 46 to base flange 20 in a longitudinally extending vertical central plane. One upstanding side arm 47 has its top end rigidly connected to a first rigid pressure pad 48 via a lateral extension 50 and a stem member 49, and the other upstanding side arm 51 has its top end rigidly connected to a second rigid pressure pad 52 via a lateral extension 53 and a stem member 54. Pressure pads 48 and 52 are generally parallel to upstanding bracket 19 and are alternately engageable with symmetrically opposite side portions of a plasma transfusion bag 25 mounted between the glass plates 18, 24 responsive to the oscillation of the U-shaped member 60 around its vertically extending pivotal axis at 46. To provide such oscillation, the outer end portion of lateral extension 53 is connected by a link bar 55 to a crank disc 56 driven by a motor 57 mounted vertically on a corner tab portion 58 provided on flange 20 (see FIG. 6).

A cycle of operation consists of (1) insertion of a transfusion bag 25 between the parallel glass plates 18, 24; (2) clamping the bag by adjusting the position of the bracket member 19 to a condition such as shown in FIG. 2, wherein flow is substantially restricted to the space between the parallel plates 18, 24, this position being maintained by tightening the clamping screws 21, 21 after the proper position of the bracket 19 has been established; and (3) energizing the motor 57 to cause periodic compression and release of alternate side portions of the bag 25, which results in laminar flow and maximal orientation face-on to the laser beam 15 of the discoidal platelets every half cycle. (4) The signal generated by the photodiode 37 and duly processed in processor 42 at such maximal orientation during 10 seconds of periodic compression is averaged (as shown at $I_1$ in FIG. 5); (5) the compression is stopped by deenergizing motor 57, leading to a gradual randomization of platelet orientation by Brownian diffusion, whereby the output signal gradually diminishes, as shown at 60 in FIG. 5; and (6) 30 seconds after cessation of flow a 5-second average $I_0$ is obtained for the randomly oriented platelets. Utilizing a computer program based on a multiple-scattering theory (Robert F. Bonner, "Quantitative Application of Multiple-Scattered Light to Non-Invasive Clinical Testing", Biophysical Journal, Feb. 1982) and empirical data, the $I_0$ value is used to obtain the platelet concentration within the bag. Similarly, the fractional change of signal intensity on orienting the platelets $(I_1 - I_0)/I_0$ is used to compute the fraction of discs. The computations are performed in the computer 43, and the computed numbers are read out on the display/printout unit 44, after which the above cycle may be repeated for the next transfusion bag to be tested.

A suitable programmable controller 61 may be employed for providing automatic sequential control of the various mechanical and electronic parts of the apparatus 11, as is diagrammatically illustrated in FIG. 1.

While a specific embodiment of an improved system for the optical assessment of platelet viability in blood plasma has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. An apparatus for assessing the viability of platelets in a transparent flexible blood storage bag comprising a support, a collimated light source providing a beam defining an optical axis, means on said support for clampingly receiving a blood storage bag in a position substantially transverse to said axis such as to allow said beam to traverse the bag and to be scattered by platelets in the bag, means for aligning platelets within said bag substantially face-on with respect to said beam, light gate means in the path of scattered light and limiting transmission thereof to a predetermined scatter angle relative to said optical axis, photoelectric sensing means, means to direct the transmitted scattered light to said photoelectric sensing means, whereby to generate an electrical signal in accordance with the state of the platelets in the bag, and means to measure said signal.

2. The platelet assessment apparatus of claim 1, and wherein said means for aligning platelets comprises means to periodically compress a portion of the bag to produce laminar flow of fluid in the bag transverse to said optical axis.

3. The platelet assessment apparatus of claim 1, and wherein said light gate means has an annular light gate aperture coaxial with said beam, defining said predetermined scatter angle.

4. The platelet assessment apparatus of claim 1, and wherein said means for clampingly receiving the plasma bag includes transparent parallel abutment means engageable on opposite sides of the bag to define a restricted flow space therebetween.

5. The platelet assessment apparatus of claim 4, and wherein said abutment means comprises respective transparent glass plates engageable with said opposite sides of the bag.

6. The assessment apparatus of claim 1, and wherein said means for aligning platelets comprises means to alternatively periodically compress and release opposite outer portions of the bag to produce laminar flow of fluid in the bag transverse to said optical axis.

7. The platelet assessment apparatus of claim 6, and wherein said means to alternately compress and release said outer portions of the bag comprises an oscillatory member pivotally mounted on said support, said oscillatory member having respective opposite pressure elements engageable with said outer bag portions responsive to oscillation of the oscillatory member, and oscillating drive means coupled to said oscillatory member.

8. The platelet assessment apparatus of claim 7, and wherein said oscillating drive means comprises a motor-driven crank member and link means drivingly connecting said crank member to said oscillatory member.

9. The platelet assessment apparatus of claim 1, and means to periodically compress a portion of the bag to produce laminar fluid flow in the bag transverse to said optical axis, whereby to align platelet discs substantially face-on with respect to said beam and correspondingly modify the intensity of the scattered light transmitted to said photoelectric sensing means, correspondingly increasing the strength of said electrical signal.

10. The platelet assessment apparatus of claim 9, and means to compute the quantities $I_0$ and $(I_1 - I_0)/I_0$, wherein $I_1$ represents an average signal generated while said bag portion is periodically compressed and $I_0$ represents a steady state signal generated after a sufficient stoppage of said periodic bag compressing means to allow the platelets to become randomly oriented.

11. A method of assessing the viability of blood platelets contained in a transparent flexible bag, comprising inserting the bag substantially transversely in the path of a collimated light beam, locally constricting the bag in the region of the beam to define a relatively restricted fluid flow path, manipulating the bag by periodically squeezing and releasing an outer portion of the bag to produce laminar fluid flow and face-on orientation to the beam of discoid platelets in the plasma where the beam traverses the bag, whereby to cause scattering of the beam by such discoid platelets, and comparing the intensity of the scattered light at a selected scattering angle to the beam axis with the intensity of the scattered light at this angle obtained when the plasma platelets are substantially randomly oriented.

12. The platelet assessment method of claim 11, and wherein the manipulation of the bag comprises periodically compressing and releasing an outer portion of the bag laterally spaced from said restricted fluid flow path.

13. The platelet assessment method of claim 11, and wherein the manipulation of the bag comprises alternately periodically compressing and releasing opposite outer portions of the bag.

14. The platelet assessment method of claim 11, and wherein the manipulation of the bag comprises alternately periodically compressing and releasing opposite lateral outer portions of the bag for a predetermined time period.

15. A method of assessing the viability of blood platelets contained in a transparent flexible bag comprising inserting the bag in the path of a collimated light beam, constricting the bag in the region of the beam to define a relatively restricted fluid flow path, manipulating the bag by periodically compressing and releasing an outer portion of the bag to produce laminar fluid flow and face-on orientation to the beam of discoid platelets in the plasma where the beam traverses the bag, whereby to cause scattering of the beam by such discoid platelets, directing the scattered light at a selected scattering angle relative to the optical axis of the beam to a photoelectric sensing element to generate an electrical signal, and comparing this generated signal to that obtained when the plasma platelets are substantially randomly oriented.

16. The platelet assessment method of claim 15, and wherein the manipulation of the bag comprises periodically compressing and releasing an outer portion of the bag for a predetermined time period.

17. The platelet assessment method of claim 15, and wherein the manipulation of the bag comprises alternately periodically compressing and releasing opposite outer portions of the bag for a predetermined time period.

* * * * *